(12) United States Patent
Rapp

(10) Patent No.: US 6,566,581 B1
(45) Date of Patent: May 20, 2003

(54) TRANSGENIC NON-HUMAN MAMMALS WITH AN ONCOGENIC MUTANT OF RAF-1 GENE

(76) Inventor: Ulf R. Rapp, Versbacher Strasse 5, D-97078 Würzburg (DE)

(*) Notice: Subject to any disclaimer, the term of this patent is extended or adjusted under 35 U.S.C. 154(b) by 0 days.

(21) Appl. No.: 09/555,279

(22) PCT Filed: Nov. 27, 1998

(86) PCT No.: PCT/DE98/03557
§ 371 (c)(1),
(2), (4) Date: Jul. 21, 2000

(87) PCT Pub. No.: WO99/28453
PCT Pub. Date: Jun. 10, 1999

(30) Foreign Application Priority Data

Nov. 28, 1997 (DE) .......................................... 197 54 774

(51) Int. Cl.[7] .......................... G01N 33/00; A01K 67/00; C12N 15/00; C07H 21/04; C12Q 1/00
(52) U.S. Cl. .............................. 800/3; 800/18; 800/25; 536/23.1; 536/23.2; 435/4; 435/320.1; 435/455
(58) Field of Search ................................ 800/8, 14, 18, 800/21, 25, 3; 435/320.1, 455, 4; 536/23.1, 23.5, 24.1, 23.2

(56) References Cited

PUBLICATIONS

Wall, R.J.; Transgenic Livestock : Progress and Prospects for the Future, 1996, Theriogenology 45: 57–68.*
Mullins et. al.; Perspective Series : Molecular Medicine in Genetically Engineered Animals, 1996, J. Clin. Invest. vol. 98, No. 11: S37–S40.*
Kappel et. al.; Regulating gene expression in transgenic animals , 1992, Current Opinion in Biotechnology 3: 548–553.*
Houdebine, L–M; Production of pharmaceutical proteins from transgenic animals, 1994, Journal of Biotechnology 34: 269–287.*
Hammer et. al.; Genetic Engineering of Mammalian Embryos, 1986, J. Anim. Sci 63: 269–278.*
Strojek et. al.; The Use of Transgenic Animal Techniques for Livestock Improvement, 1988, Genetic Engineering: Principles and Methods, vol. 10: 221–246.*
Ngo et. al.; Computational Complexity, Protein Structure Prediction, and the Levinthal Paradox, 1994. In: The Protein Folding Problem and Tertiary Structure Prediction (Merz et al., eds) Birkhouser, Boston, pp. 491–495.*
Rudinger; Characteristics of the amino acids as components of a peptide hormone sequence, 1976. In: Peptide Hormones (Parsons, J.A., ed.), University Park Press, Baltimore, pp. 1–7.*

* cited by examiner

Primary Examiner—Dave T. Nguyen
Assistant Examiner—Quang Nguyen
(74) Attorney, Agent, or Firm—McGlew and Tuttle, P.C.

(57) ABSTRACT

The invention relates to a transgenic non-human mammal whose cells express a constitutively active oncogenic mutant of the kinase-domain of the Raf-1 gene or a protein coded by a corresponding normal allele or derivative of the A, B or c-Raf-1 gene.

7 Claims, 3 Drawing Sheets

TRANSGENIC NON-HUMAN MAMMALS WITH AN ONCOGENIC MUTANT OF RAF-1 GENE

FIELD OF THE INVENTION

The invention relates to a transgenic non-human mammal, to a method for producing the latter, to the utilization thereof, to a cell tissue therefrom, to a method for producing such cell tissue, to the utilization thereof, to a recombinant DNA expression vector and to the utilization of such vector.—The term non-human mammal refers to taxonomically higher units than animal species. Transgenic animals are organisms carrying an additional gene not originating from their species, that is a foreign gene in their genome. For the purpose of the invention in particular such transgenic animals are meant that have the foreign gene also in the germ cells, that is which hand on the foreign gene vertically, i.e. from generation to generation. If a special transgenic animal has been created, further corresponding transgenic animals may be obtained by breeding. The transgenic animals are known in the art in various embodiments, and various methods for producing transgenic animals are also known. As an example only, reference is made to document R. Jaenisch, Science, Vol. 240, 10, 1988, page 1468 ff., and the documents cited therein. The term cell tissue comprises complete organs or parts of organs of an animal, however also specific cell lines that can be isolated and cultivated therefrom, i.e. Increased in number.

A recombinant DNA expression vector is an instrument for producing a transgenic animal carrying, among other features, the foreign DNA to be integrated in the cells of the animal.

BACKGROUND OF THE INVENTION

The general technological background of the special transgenic animal provided by the invention is the following. Cancer, in particular lung cancer, is one of the most widespread diseases of mankind, and has up to now therapy predictions offering little success only. In the framework of the development of better therapies for cancer diseases it is, among other conditions, required and also legally laid down, for ethical reasons, to perform pre-clinical examinations in animals models with possible active substances obtained from basic research or by screening tests. In the case of examinations of prospective active substances for cancer therapies, it is therefore required to provide animals or (animal) cell tissues having the respective cancer diseases to be investigated, in order that the physiological effects, possibly also side effects, of the active substances can be tested in a qualitative and quantitative manner.

Cancer diseases are caused in many cases by the effects of so-called oncoproteins. These are proteins that have different structures compared to corresponding proteins in a healthy organism. These oncoproteins are capable, through not yet fully understood processes, to transform normal cells into uncontrollably proliferating cells, i.e. cancer cells. The formation of oncoproteins in an organism is in turn caused by so-called oncogenes, i.e. genes coding for the oncoprotein. Oncogenes may be introduced into a cell by viruses, may however also be formed by way of mutation of (certain) "healthy" genes, the proto-oncogenes. Such mutations can for instance take place by translocation (displacement) of a gene responsible for the production of a protein within the genome, by point mutations (replacement of a base and/or individual bases in the DNA of a gene responsible for the production of a protein by different base, with the consequence of the formation of a protein of modified amino acid sequence, the oncogene), by deletion (removal of one or more bases) or also by mutations in the region of a so-called promoter applicable for the respective gene. As a promoter is designated a DNA region of a gene by means of which the transcription (of the DNA code into a corresponding RNA) and thus finally also the expression (formation) of the protein correlated with the gene can be controlled. In a natural manner, a specific promoter is usually assigned to each gene, this promoter being arranged ahead of the latter in the genome. Ahead means that the promoter in the DNA sequence has a certain distance to the starting point of a transcription. For initiating a transcription, it is then also required that so-called transcription factors (often specific for the cell type) are taken up by the promoter.

In particular in connection with lung cancer, the so-called Raf proto-oncogenes play a special role. These genes are highly conservative with regard to evolution, and code kinases specific for serine/threonine of the cytoplasm playing in turn a role in the mitogenic signal transduction. Known in the art are for instance the genes A, B and c-Raf-1. For a survey, reference is made to documents U. R. Rapp et al., The Oncogene Handbook, Elsevier Science Publishers, Netherlands, page 115–154, 1988, and U. R. Rapp, Oncogene, 6, 495, 1991. To the family of the Raf genes belongs, among others, the c-Raf-1 gene expressing the c-Raf-1 kinase ubiquitarily in an organism. The c-Raf-1 gene comprises three conserved regions, i.e. these regions are in accordance with corresponding regions of other Raf genes of the family. The region CR1 is a regulatory domain around a cys finder consensus sequence, the region CR2 is a region having a high content of serine or threonine, and CR3 is the kinase domain. With regard to further detailed information, reference is made to document U.S. Pat. No. 5,618,670. From this document are also known (partial) sequences of the natural form of the CR3 region of the c-Raf-1 gene of mice and (partial) sequences of various point mutations thereof. From document U.S. Pat. No. 5,156,841 are known plasmids and eucariotic expression vectors containing A-Raf and v-Raf oncogenes, however in different connections, namely the genic production of Raf oncoproteins for immunological investigations.

DETAILED DESCRIPTION OF THE INVENTION

The invention is based on the technical problem to provide non-human mammals in sufficiently high number and with a pathology being uniform and reproducible with regard to tumor formation, for the purpose of pre-clinic examinations of prospective anti-cancer substances or therapies.

For achieving this object, the invention teaches a transgenic non-human mammal whose cells express a constitutively active oncogenic mutant of the kinase-domain of the c-Raf-1 gene or a protein coded by a corresponding normal allele or a derivative of the A, B or c-Raf-1 gene. —The term constitutively active means, in the context of the invention, that the protein per se is always active, i.e. the physiological effect of the protein is always obtained even without the condition of further reaction cascades in a cell or an organism. In contrast thereto, the activation of the not constitutively active Raf-1 protein requires for instance the bonding of the Ras protein with the Raf-1 protein. The term constitutively active therefore refers, for the purpose of the invention, only to the protein or the corresponding gene code and not to the gene itself or the gene activation. The reference to the Raf-1 gene means Raf-1 genes or variants thereof existing in any organism, at least however such Raf-1 genes existing in mammals. By the fact that the mammal is a transgenic animal having the mentioned features, identical animals, with regard to the pathology of the tumors induced by the expression of the mutant, can be obtained in any number by way of the natural reproduction from a transgenic base animal. Thereby pre-clinic examinations of active substances or therapies can be performed with the required reproducibility and the required statistical significance, and that also with defined control groups.

For performing pre-clinic examinations of active substances and therapies against lung cancer it is recommended that the expression of the protein coded by the constitutively active oncogenic mutant of the kinase-domain of the c-Raf-1 gene or by a corresponding allele or a derivative of the A, B or c-Raf-1 gene takes place in lung cells, since then the animals develop reproducible lung tumors.

In structural regard, a mammal as described above is characterized by that it contains foreign DNA with constitutively active oncogenic mutant of the kinase-domain of the c-Raf-1 gene or with a corresponding normal allele or a derivative of the A, B or c-Raf-1 gene. Alleles or derivatives are variants in a DNA sequence virtually not affecting the basic function of the respective gene.

Advantageously, the foreign DNA in addition contains a promoter for the surfactant protein C, preferably for the human surfactant protein C, and this promoter is arranged in the foreign DNA with the proviso that by the promoter the transcription of the mutant of the kinase-domain of the c-Raf-1 gene or of a corresponding normal allele or a derivative of the A, B or c-Raf-1 gene is controlled. In other words, the promoter being in a natural manner arranged ahead of the gene coding the surfactant protein C, is arranged instead, according to the invention, at a suitable position of the mutant or of the gene. The precise arrangement of promoter and mutant or gene with regard to each other is usual knowledge of the man skilled in the art. If the exact positioning of the special promoter ahead of the gene utilized according to the invention cannot be derived from basic considerations, simple tests with different variants of positioning can however be performed, in order to determine a suitable position. The number of variants in question, under consideration of the general technical knowledge, is however very limited. The surfactant protein C plays a role for the surfactant factor reducing the alveolar surface tension between the lung epithelium and air and thus preventing that the alveoli will collapse during breathing-out and that the epithelia with stick together. By application of the promoter for the surfactant protein C it is achieved that only the transcription factors specifically or with increased frequency occurring in the lung and inter-reacting with this promoter can so to speak switch on the mutant, with the result that lung tumors will be formed at high selectivity and reproducibility.

In a preferred further embodiment of the invention, the foreign DNA in addition contains DNA of the SV40 virus, SC means Simian Virus. This comprises the polyadenylation sequence and intron/exon regions of the SV40 virus being known in the art (see description of the following FIG. 1). The integration of this SV40 DNA causes an increase of the translation efficiency of the polyadenylated mRNA. In detail it is preferred that the mammal comes from the group of rodents.

A transgenic non-human mammal as described above is obtainable by the following steps: a) integration of the cDNA sequence of a constitutively active oncogenic mutant of the kinase-domain of the c-RAF-1 gene or of a corresponding normal allele or a derivative of the A, B or c-Raf-1 gene in an expression vector, b) insertion of the transgenic vector obtained in step a), preferably after linearization, in pronuclei of fertilized oocytes from a non-human mammal, c) implantation of the oocytes obtained in step b) in brood animals of the same species as the donor species of the oocytes and delivery of descendant animals from the oocytes, d) genotypization and selection of the descendant animals obtained in step c) with the proviso that cells of the selected mammals express a constitutively active oncogenic mutant of the kinase-domain of the c-Raf-1 gene or a protein coded by a corresponding normal allele or a derivative of the A, B or c-Raf-1 gene. Genotypization can be obtained by means of methods well known to the man skilled in the art, for instance by tail biopsy by means of PCR (polymerase chain reaction, a method for the in-vitro amplification of a defined DNA fragment) and Southern Blot (a method for the analysis of DNA fragments in DNA preparations), with those mammals being selected whose cells can be proven by the examinations of the genotypization to contain the foreign DNA according to the invention. Advantageously, the expression vector used is step a) contains a promoter for the surfactant protein C, preferably a promoter for the human surfactant protein C. This promoter is arranged in the foreign DNA with the proviso that by the promoter the transcription of the mutant of the kinase-domain of the Raf-1 gene or of a corresponding normal allele or derivative of the A, B or c-Raf-1 gene is controlled. In detail, the foreign DNA may comprise for instance either the healthy (FIG. 1) or a constitutively active oncogenic mutant of the Raf-1 gene with a sequence according to one of FIG. 1, however with deletion as ΔRaf (26-302). In place of a deletion, point mutations of the sequence shown in FIG. 1 can also be used. Such point mutations can for instance specifically be caused by administration of 1-ethyl-1-nitrosourea (ENU) to animals having the healthy sequence, thereby such mutants being accessible in a simple manner.

The invention also relates to a method for producing a transgenic non-human mammal. Non-human mammals according to the invention are used for pre-clinic examinations of the effectiveness of substances directed against lung carcinomas and/or therapeutical methods directed against lung carcinomas, in particular for the pre-clinic examination of the effectiveness of substances inhibiting Raf-kinase. Such substances completely inhibit or reduce the activity of Raf-kinases, thereby possibly a means for the deactivation particularly of Raf-oncoproteins and therefore for the proliferation inhibition of tumor cells being found. Another advantageous utilization of a non-human mammal according to the invention is the investigation of the pathogenesis of lung tumors, thereby a better understanding of the disease per se being possible.

The invention however also relates to cell tissues, in particular lung tissues, from a transgenic non-human mammal, which cell tissue has a higher probability of tumor formation, preferably of lung tumors, to a method for the production thereof and to the utilization thereof. With regard to the cell tissue or also specific cell lines comprised therein, isolated and possibly cultivated therefrom, all general explanations given above apply in corresponding manner.

Finally the invention also comprises a recombinant DNA expression vector containing A) the DNA sequence of a constitutively active oncogenic mutant of the kinase-domain of the c-Raf-1 gene or of a corresponding normal allele or a derivative of the A, B or c-Raf-1 gene, B) a promoter domain for the surfactant protein C, by means of which the transcription of the DNA sequence defined in A) is controllable, C) as an option the DNA sequence of the SV40 virus. By means of such a vector the transgenic mammals according to the invention and possibly also the cell tissues therefrom can be produced. As an example, the DNA sequence defined in A) comprises a sequence according to FIG. 4 or to the end of the specification, respectively, or a sequence ΔRaf (26-302) derived therefrom, and/or the promoter domain defined in B) is a promoter domain for the human surfactant protein C. The reproduced sequence is that of human-c-Raf-1. Instead, also the c-Raf-1 sequences of the mouse, wild type or mutated, according to document U.S. Pat. No. 5,618,670 can be used. Other sequences, even from other organisms, are also possible, as far as they are basically a Raf-1 sequence.

Subject matter of the invention is further a screening method with utilization of the transgenic non-human mammals according to the invention or of cell tissues therefrom, a group of prospective active substances against cancer, in particular lunger cancer, being administered to the animals, and an evaluation of the effects of each individual prospective active substance with regard to proliferation inhibition, oncoprotein inhibition or the like is performed. The invention further comprises active substances that can be detected by such a screening method as being sufficiently effective.

Plasmids with transgenic vectors according to the invention (active oncogenic mutant of the kinase-domain of the human c-Raf-1 gene, i.e. plasmid SPC-ΔRaf (26-302) and a transgenic vector with normal human c-Raf-1 gene, i.e. plasmid SPC-Raf-1) were registered at DSMZ—Deutsche Sammlung von Mikroorganismen and Zellkulturen GmbH, Mascheroder Weg 1b, D-3812 Braunscheweig. The registration number for the plasmid SPC-ΔRaf (26-302) is 11849. Thus the invention also relates to transgenic vectors as registered, as well as to transgenic animals or cells or cell tissues to be produced therefrom, and to the utilizations described above of such animals or cells or cell tissues.

BRIEF DESCRIPTION OF THE DRAWINGS

In the following, the invention will be described by figures and embodiments representing examples only. There are.

DNA sequence (linear) of the kinase-domain of the human-c-Raf-1 gene (SEQ ID NO:1).

EXAMPLES

The general procedure during the production of transgenic mice according to the invention was the following. The cDNA sequences of the transforming c-Raf subdomain (Raf B×B) were cloned into a lung-specific expression vector containing the promoter region of the human surfactant-associated protein C (SPC). After restriction digestion and linearization of these transgenic vectors schematically shown in FIG. 2, the respective foreign DNA was inserted into the pronuclei of fertilized oocytes, then implanted into brood mice. The descendants of such mice were genotyped by tail end biopsy by means of PCR and Southern Blot. By the thus identified founder animals, mouse lines were established, in whose lungs the expression of the transgene was detected in Western or Northern Blot or by means of RT-PCR.

Figure 1:
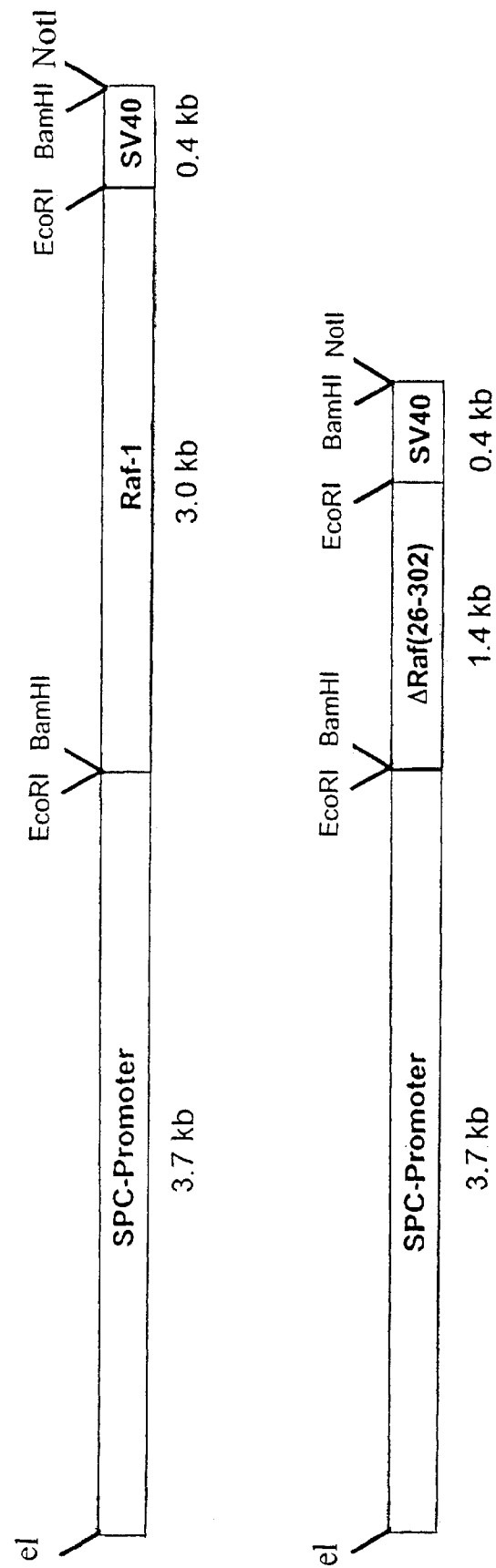
FIG. 1 a schematic representation of the structure of vectors suitable for the invention, FIG. 2 Southern Blot of selected transgenic animals according to the invention, FIGS. 3A–3B Western or Northern Blot, respectively, of obtained animal lines according to the invention.

FIG. 1 shows lung-directed expression vectors for the protein kinase Raf-1. The transgenic vectors include the 3.7 kb (kilobases) wide region of the human SPC promoter, the 3.0 kb c-Raf-1 or 1.4 kb human ΔRaf (26-302) cDNA fragments and a 0.4 kb fragment of viral DNA including the polyadenylation sequence and intron/exon regions of the SV40 virus, thereby the translation efficiency of the polyadenylated mRNA being increased. Further are drawn the intersections of the used (also in the following examples) restriction endonucleases.

The individual steps of the exemplary general procedure described above are explained with regard to the experimental measures in detail in the following examples.

Example 1

Cloning of the cDNA sequences of the transforming c-Raf subdomain into a lung-specific expression vector was performed as follows. The vector SPC-Raf-1 for generating the wild type-Raf-1 transgenic mice was produced by that a 3.0 kb fragment of the human Raf-1 cDNA (Bonner, T. I.; Oppermann, H.; Seebrug, P.; Kerby, S. B.; Gunnell, M. A.; Young, A. C.; and Rapp, U. R.; 1986; "The complete coding sequence of the human raf oncogene and the corresponding structure of the c-raf-1 gen."; Nucleic Acids Res.; 14, 109) was cloned in the EcoRI interface of the plasmid SPC3.7/5V40 including the 3.7 kb promoter region of the human surfactant-associated protein C (SPC) (Korfhagen, T. R.; Glasser, S. W.; Wert, S. E.; Bruno, M. D.; Daugherty, C. C.; McNeish, J. D.; Stock, J. L.; Potter, S. S.; Whitsett, J. A.; 1990; "Cis-acting sequences from a human surfactant protein gene confer pulmonary-specific gene expression in transgenic mice."; Proc. Natl. Acad. Sci.; 87, 6122). In analogous manner, the transgenic vector SPC-ΔRaf (26-302) was cloned by insertion of a 1.4 kb fragment of human Raf-1 cDNA that has been obtained by deletion of the amino acids 26 to 302 of the regulatory domain (Bruder, J. T.; Heidecker, G.; and Rapp, U. R.; 1992; "Serum-, TPA-, and Ras-induced expression from Ap-1/Ets-driven promoters requires Raf-1 kinase."; Genes and Dev.; 6, 545) and thus contains the kinase-domain of the Raf-1 protein (activated oncogenic mutant of the Raf-1 kinase).

Example 2

The linearization and the pronucleus injection were performed as follows. The transgenic vectors were cut with the restriction endonucleases NotI and NdeT, cleaned with a preparative agarose gel (Sambrooks et al., 1989, see below), and diluted to a concentration of 1 ng/ml. 200 ng of the linearized DNA fragments were injected into the male pronuclei of fertilized oocytes. Transgenic founder mice were identified by analysis of the genomic DNA isolated from tail ends by Southern Blot (see also example 3). The founder mice were crossed with non-transgenic B6D2 mice, in order to establish stable lines.

The used mice were C57BL/6×DBA F2 mice (B6D2 mice), and were obtained from Harlan Winkelmann (Borchen) and from Charles River (Sulzfeld), and were held and bred on in the stable of the MSZ (Institut für Medizinische Strahlenkunde und Zellforschung, Würzburg University, D-9708 Würzburg) under pathogen-free conditions.

Example 3

Figure 2:
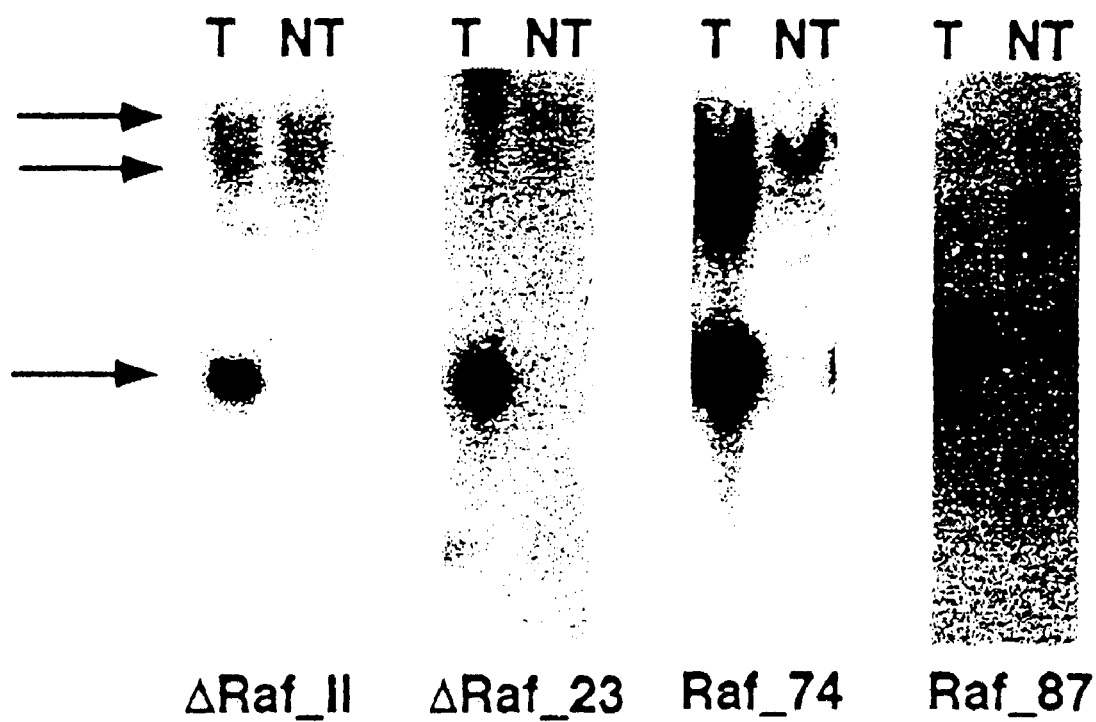

PCR and Sourthern Blot for genotypization were performed by the following operational instructions. For the detection of the transgenic integration, 10 μg genomic DNA from tail ends were cut over night with 40 units BamHI, separated on a 0.7% agarose gel by means of electrophoresis, and transferred by means of a capillary blot to nitrocellulose (Sambrook, J.; Fritsch, E. F.; Maniatis, T.; "Molecular Cloning: a laboratory manual)"; Cold Spring Harbor Laboratory Press). After fixation of the DNA by u.v. light followed the detection of the transgene by hybridization of the membrane (Church, G. M. and Gilbert, W.; "Genomic sequencing"; Proc. Natl. Acad. Sci.; 81, 1991) with a Raf-1 probe (containing the Raf-1/SV40 sequence) that was obtained by digestion of the transgenic vector SPC-Raf-1 with BamHI. The bound probe cross-hybridizing also with the mouse-Raf locus, was detected by exposure of the membrane on film material, and marked a 3.4 kb Raf-1/SV40 fragment or a 1.8 kb ΔRaf (26-302)/SV40 fragment, respectively. The result of Southern Blots from selected animals according to the invention is shown in FIG. 2. Therein the positions of endogenic Raf-1 and the transgenic ΔRaf (26-302) or Raf-1 fragments in transgenic (T) and non-transgenic (NT) mice for two independent mouse lines (ΔRaf_11 and ΔRaf_23 or Raf_74 and Raf_87, respectively) can be seen. The positions of the respective fragments are identified by arrows. It can easily be found that the bands to be assigned to transgenic ΔRaf (26-302) or Raf-1 fragments, respectively (lower arrows), are only registered for the transgenic animals.

Example 4

In total 2 c-Raf-BxB (or ΔRaf (26-302), respectively) mouse lines were obtained. These mice according to the invention of both lines developed at an age of 6 to 7 months massive lung carcinomas, the cellular origin of which corresponds with regard to distribution pattern and phenotype to the pneumocytes type II. Investigations of the time dependence of the tumor development showed that after 2 months already significant multi-centric tumor formation occurred. In the lung tissue of both lines could also be detected the expression of the transgene in Western Blot, as visible in FIG. 3. Thus also the correlation between specific misapplied Raf kinase activity and lung tumor induction is proven in vivo.

Figure 3A:
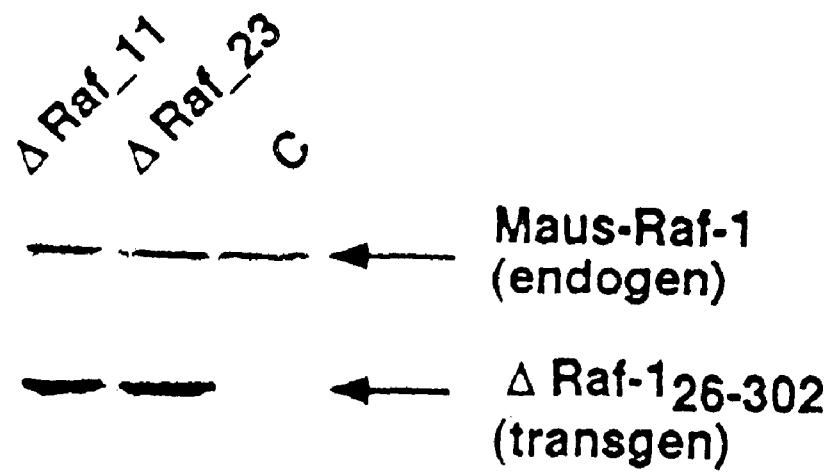
Figure 3B:
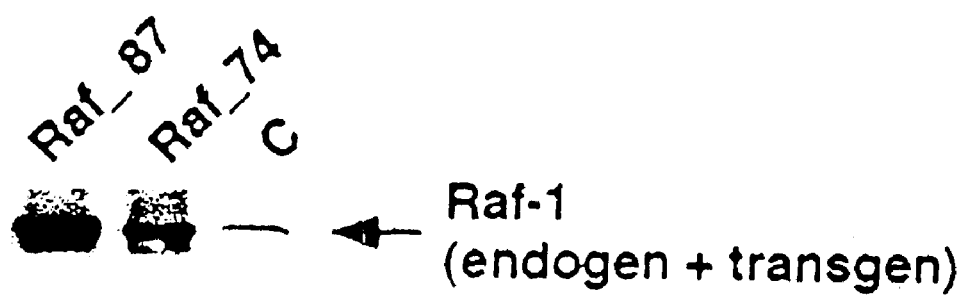

The Western Blot of FIG. 3 was obtained as follows. The protein expression of the transgene was detected by that lung tissue of the mice was lysated in detergent containing buffer, and approx. 100 μg of the solubilized proteins were split with a 10% SDS polyacrylamid gel. After transfer of the proteins to nitrocellulose, the membrane was incubated over night with milk-powder containing blocking solution and successively for 1 hour each with a polyclonal anti-Raf-1 rabbit anti-serum and the peroxidase-coupled anti-rabbit immunoglobulin. After each incubation step, several times washing solution was employed. The detection of the bound anti-bodies took place by the reaction of the peroxidase with a chemiluminescene emitting substrate and exposure on film material. In FIG. 3 is shown in detail an immuno blot with solubilized proteins from lung tissue of the specified mouse lines and from non-transgenic control mice (C) after staining with the anti-Raf rabbit anti-serum. Specified are the positions of the respective Raf proteins at approx. 74 kDa (Raf-1) and 42 kDa (ΔRaf (26-302)). In FIG. 3a is identified the endogenic Raf-1 of the mouse and the ΔRaf (26-302) in the transgenic mouse lines. In FIG. 3b can be seen, due to the identical molecular weight of endogenic murine Raf-1 and transgenic human Raf-1, the transgenic expression caused by the increase in intensity of the Raf-1 band.

The DNA sequence (linear) of the kinase-domain of the human-c-Raf-1 gene is as follows.

What is claimed is:

1. A transgenic mouse whose genome comprises a nucleic acid construct comprising a surfactant protein C promoter operably linked to a DNA sequence encoding a constitutively active oncogenic c-Raf-1 kinase mutant, wherein the c-Raf-1 kinase mutant is a c-Raf-1 kinase in which amino acids 26 to 302 are deleted, and wherein said transgenic mouse develops lung carcinomas.

2. The transgenic mouse according to claim 1, wherein said nucleic acid construct contains SV40 DNA sequences.

3. The transgenic mouse according to claim 1, wherein said promoter is human surfactant protein C promoter.

4. A method for producing a transgenic mouse having lung carcinomas, comprising the steps:
   a) preparing an expression cassette comprising a surfactant protein C promoter operably linked to a DNA sequence encoding a constitutively active oncogenic c-Raf-1 kinase mutant, wherein the c-Raf-1 kinase mutant is a c-Raf-1 kinase in which amino acids 26 to 302 are deleted;
   b) inserting the expression cassette of step a) into pronucleic of fertilized oocytes from a mouse;
   c) implanting the oocytes of step b) in brood mice, and delivery of mice which develop from the implanted oocytes; and
   d) genotyping and selecting a mouse of step c) expressing said constitutively active oncogenic c-Raf-1 kinase mutant,
   wherein said transgenic mouse develops lung carcinomas.

5. A method for screening the effectiveness of a candidate substance against lung carcinomas, said method comprises the steps of:
   a) administering said substance to the transgenic mouse of claim 1,
   b) evaluating the effectiveness of said substance in inhibiting the proliferation of lung carcinomas or in inhibiting the activity of the oncogenic c-Raf-1 kinase mutant in the transgenic mouse of step a) copared to an untreated transgenic mouse of claim 1.

6. A method for producing a lung carcinomas tissue from a transgenic mouse having lung carcinomas, comprising the steps:
   a) preparing an expression cassette comprising a surfactant protein C promoter operably linked to a DNA sequence encoding a constitutively active oncogenic c-Raf-1 kinase mutant, wherein the c-Raf-1 kinase mutant is a c-Raf-1 kinase in which amino acids 26 to 302 are deleted;
   b) inserting the expresson cassette of step a) into pronuclei of fertilized oocytes from a mouse;
   c) implanting the oocytes of step b) in brood mice, and delivery of mice which develop fro the implanted oocytes;
   d) genotyping and selecting a mouse of step c) expressing said constitutively active oncogenic c-Raf-1 kinase mutant; and
   e) harvesting a lung carcinoma tissue froma mouse of step d), wherein said lung carcinoma tissue expresses said oncogenic c-Raf-1 kinase mutant.

7. A method for screening the effectiveness of a candidate substance against lung carcinomas, said method comprises the steps of:
   a) applying said substance to a lung carcinoma tissue obtained from the transgenic mouse of claim 1; and
   b) evaluating the effectiveness of said substance in inhibiting the proliferation of lung carcinomas or in inhibiting the activity of the oncogenic c-Raf-1 kinase mutant in the lung carcinoma tissue of step a) compared to an untreated lung carcinomas tissue obtained from the transgenic mouse of claim 1.

* * * * *

SEQUENCE LISTING

```
<160> NUMBER OF SEQ ID NOS: 1

<210> SEQ ID NO 1
<211> LENGTH: 2977
<212> TYPE: DNA
<213> ORGANISM: human
<220> FEATURE:
<221> NAME/KEY: exon
<222> LOCATION: (105)..(105)
<221> NAME/KEY: exon
<222> LOCATION: (337)..(337)
<221> NAME/KEY: exon
<222> LOCATION: (451)..(451)
<221> NAME/KEY: exon
<222> LOCATION: (553)..(553)
<221> NAME/KEY: exon
<222> LOCATION: (712)..(712)
<221> NAME/KEY: exon
<222> LOCATION: (811)..(811)
<221> NAME/KEY: exon
<222> LOCATION: (963)..(963)
<221> NAME/KEY: exon
<222> LOCATION: (994)..(994)
<221> NAME/KEY: exon
<222> LOCATION: (1120)..(1120)
<221> NAME/KEY: exon
<222> LOCATION: (1237)..(1237)
<221> NAME/KEY: exon
<222> LOCATION: (1324)..(1324)
<221> NAME/KEY: exon
<222> LOCATION: (1501)..(1501)
<221> NAME/KEY: exon
<222> LOCATION: (1549)..(1549)
<221> NAME/KEY: exon
```

```
<222> LOCATION: (1667)..(1667)
<221> NAME/KEY: exon
<222> LOCATION: (1798)..(1798)
<221> NAME/KEY: exon
<222> LOCATION: (1933)..(1933)

<400> SEQUENCE: 1
ccgaatgtga ccgcctcccg ctccctcacc cgccgcgggg aggaggagcg ggcgagaagc      60
tgccgccgaa cgacaggacg ttggggcggc ctggctccct cagg t ttaagaattg         115
tttaagctgc atcaatggag cacatacagg gagcttggaa gacgatcagc aatggttttg     175
gattcaaaga tgccgtgttt gatggctcca gctgcatctc tcctacaata gttcagcagt     235
ttggctatca gcgccgggca tcagatgatg gcaaactcac agatccttct aagacaagca     295
acactatccg tgttttcttg ccgaacaagc aagaacagt g g tcaatgtgcg             347
aaatggaatg agcttgcatg actgccttat gaaagcactc aaggtgaggg gcctgcaacc     407
agagtgctgt gcagtgttca gacttctcca cgaacacaaa ggt a aaaaagcacg          461
cttagattgg aatactgatg ctgcgtcttt gattggagaa gaacttcaag tagatttcct     521
ggatcatgtt ccctcacaa cacacaactt t g ctcggaagac gttcctgaag              573
cttgccttct gtgacatctg tcagaaattc ctgctcaatg gatttcgatg tcagacttgt     633
ggctacaaat tcatgagca ctgtagcacc aaagtaccta ctatgtgtgt ggactggagt      693
aacatcagac aactctta t tgtttccaaa ttccactatt ggtgatagtg gagtcccagc     752
actaccttct ttgactatgc gtcgtatgcg agagtctgtt tccaggatgc ctgttagt t     811
ctcagcacag atattctaca cctcacgcct tcaccttta cacctccagt ccctcatctg      871
aaggttccct ctcccagagg cagaggtcga catccacacc taatgtccac atggtcagca     931
ccacgctgcc tgtggacagc aggatgattg a g gatgcaattc gaagtcacag             983
cgaatcagcc t caccttcagc cctgtccagt agccccaaca atctgagccc              1034
aacaggctgg tcacagccga aaacccccgt gccagcacaa agagagcggg caccagtatc    1094
tgggacccag gagaaaaaca aaatt a ggcctcgtgg acagagagat tcaagctatt       1150
attgggaaat agaagccagt gaagtgatgc tgtccactcg gattgggtca ggctcttttg    1210
gaactgttta aagggtaaa tggcac g gagatgttgc agtaaagatc ctaaggttg         1267
tcgacccaac cccagagcaa ttccaggcct tcaggaatga ggtggctgtt ctgcgc a       1324
aaacacggca tgtgaacatt ctgcttttca tggggtacat gacaaaggac aacctggcaa    1384
ttgtgaccca gtggtgcgag ggcagcagcc tctacaaaca cctgcatgtc caggagacca    1444
agtttcagat gttccagcta attgacattg cccggcagac ggctcaggga atggac t      1501
atttgcatgc aaagaacatc atccatagag acatgaaatc caacaat a tatttctcca    1559
tgaaggctta acagtgaaaa ttggagattt tggtttggca acagtaaagt cacgctggag   1619
tggttctcag caggttgaac aacctactgg ctctgtcctc tggatgg c cccagaggtg     1677
atccgaatgc aggataacaa cccattcagt ttccagtcgg atgtctactc ctatggcatc    1737
gtattgtatg aactgatgac gggggagctt ccttattctc acatcaacaa ccgagatcag    1797
a tcatcttcat ggtgggccga ggatatgcct ccccagatct tagtaagcta             1848
tataagaact gccccaaagc aatgaagagg ctggtagctg actgtgtgaa gaaagtaaag    1908
gaagagaggc ctctttttcc ccag a tcctgtcttc cattgagctg ctccaacact         1963
ctctaccgaa gatcaaccgg agcgcttccg agccatcctt gcatcgggca gcccacactg    2023
```

-continued

```
aggatatcaa tgcttgcacg ctgaccacgt ccccgaggct gcctgtcttc tagttgactt    2083
tgcacctgtc ttcaggctgc caggggagga ggagaagcca gcaggcacca cttttctgct    2143
ccctttctcc agaggcagaa cacatgtttt cagagaagct ctgctaagga ccttctagac    2203
tgctcacagg gccttaactt catgttgcct tcttttctat ccctttgggc cctgggagaa    2263
ggaagccatt tgcagtgctg gtgtgtcctg ctccctcccc acattcccca tgctcaaggc    2323
ccagccttct gtagatgcgc aagtggatgt tgatggtagt acaaaaagca ggggcccagc    2383
cccagctgtt ggctacatga gtatttagag gaagtaaggt agcaggcagt ccagccctga    2443
tgtggagaca catgggattt tggaaatcag cttctggagg aatgcatgtc acaggcggga    2503
ctttcttcag agagtggtgc agcgccagac attttgcaca taaggcacca aacagcccag    2563
gactgccgag actctggccg cccgaaggag cctgctttgg tactatggaa cttttcttag    2623
gggacacgtc ctcctttcac agcttctaag gtgtccagtg cattgggatg gttttccagg    2683
caaggcactc ggccaatccg catctcagcc ctctcaggag cagtcttcca tcatgctgaa    2743
ttttgtcttc caggagctgc ccctatgggg cgggccgcag ggccagcctg tttctctaac    2803
aaacaaacaa acaaacagcc ttgtttctct agtcacatca tgtgtataca aggaagccag    2863
gaatacaggt tttcttgatg atttgggttt taattttgtt tttattgcac ctgacaaaat    2923
acagttatct gatggtccct caattatgtt attttaataa aataaattaa attt          2977
```